United States Patent [19]

Mericle et al.

[11] Patent Number: 5,423,837
[45] Date of Patent: Jun. 13, 1995

[54] SURGICAL KNOT PUSHER

[75] Inventors: Robert W. Mericle, Flemington; Malcolm D. Heaven, Hopewell, both of N.J.

[73] Assignee: Advanced Surgical, Inc., Princeton, N.J.

[21] Appl. No.: 165,915

[22] Filed: Dec. 14, 1993

[51] Int. Cl.⁶ ............................................. A61B 17/04
[52] U.S. Cl. .................... 606/148; 606/144; 289/17
[58] Field of Search ................ 606/1, 139, 144, 148; 289/17

[56] References Cited

U.S. PATENT DOCUMENTS

| | | | |
|---|---|---|---|
| 3,752,516 | 8/1973 | Mumma | 289/17 |
| 4,641,652 | 2/1987 | Hutterer et al. | 606/148 |
| 4,662,635 | 5/1987 | Mulhollan et al. | 606/144 |
| 4,961,741 | 10/1990 | Hayhurst | 606/139 |
| 5,084,058 | 1/1992 | Li | 606/144 |
| 5,087,263 | 2/1992 | Li | 606/144 |
| 5,176,691 | 1/1993 | Pierce | |
| 5,269,791 | 12/1993 | Mayzels et al. | |

*Primary Examiner*—Gary Jackson
*Attorney, Agent, or Firm*—Burns, Doane, Swecker & Mathis

[57] ABSTRACT

A surgical knot pusher, including a body shaft, a tip arranged on one end of the body shaft, and a slot in a sidewall of the tip for manipulating suture material extending through an opening in an endwall of the tip. A notched slit is connected to the opening and the opening has a diameter which is larger than the width of the slit. The slot may include two channels which intersect each other with a first channel of the slot parallel to a long axis of the body shaft. The surgical knot pusher may also include a blade slidable in the slot for shearing the suture material after the knot pusher is used to advance and tighten a slip knot in the suture material. The blade may be attached to an end of a spring-biased cutter shaft slidable inside the body shaft.

13 Claims, 2 Drawing Sheets

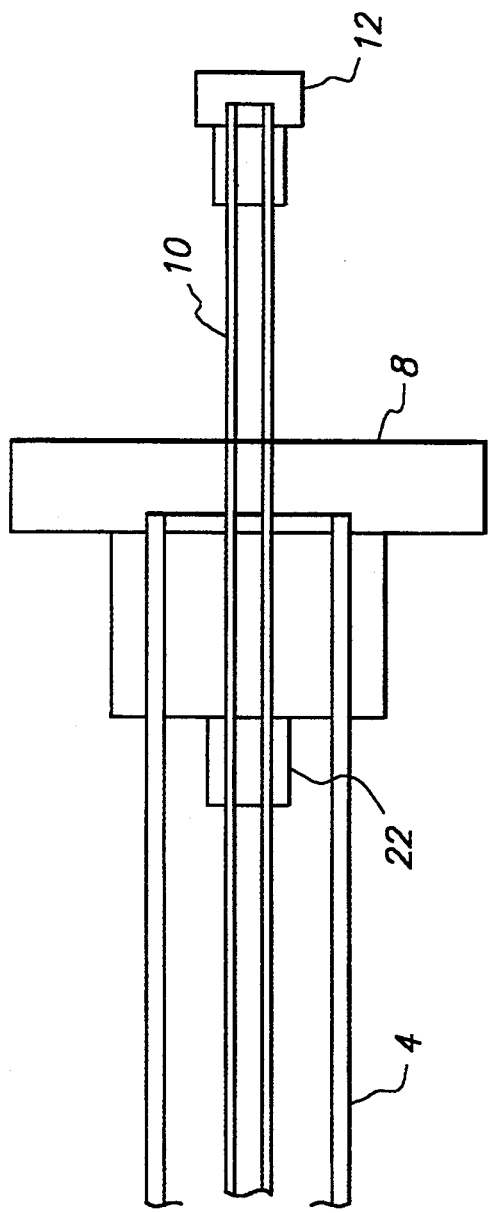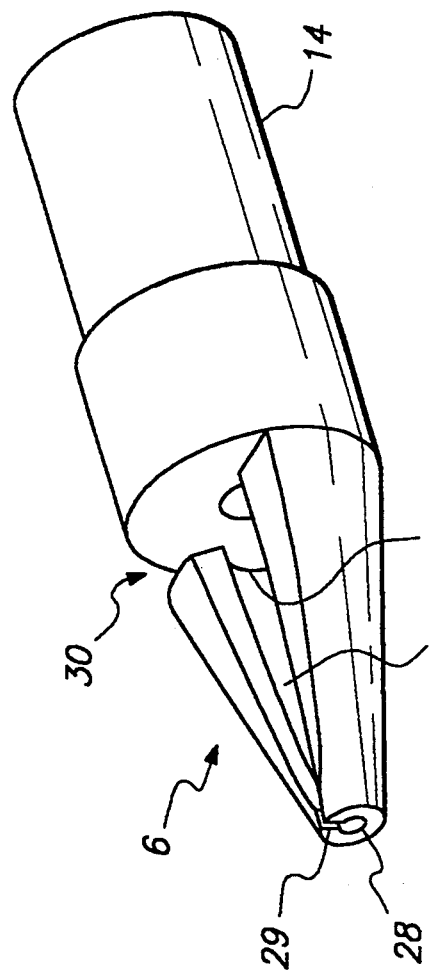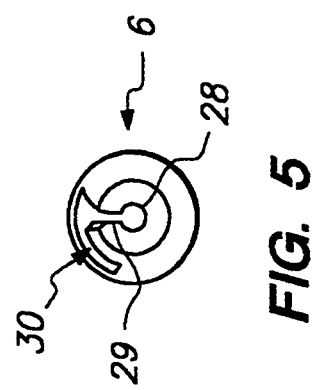

SURGICAL KNOT PUSHER

BACKGROUND OF THE INVENTION

1. Field of the Invention

The present invention generally relates to surgical knot tying and cutting tools including a suturing or ligating aid or guide. More specifically, the invention relates to a surgical knot pusher for assisting with the placement and cutting of suture knots which have been tied extracorporeally during a surgical procedure.

2. Description of the Related Art

Surgical knot placement can be a very difficult task in situations where access to the surgical site is impeded or body fluids make the suturing material difficult to handle. Each of these problems can be particularly difficult to overcome in laparoscopic procedures where surgeons must tie surgical knots inside a small access port in a patient's body using only mechanical instruments. Devices for surgical knot tying are disclosed in U.S. Pat. Nos. 3,752,516; 4,602,635; 4,961,741; 5,087,263; and 5,176,691.

In a typical laparoscopic procedure, a suture loop is stitched between two portions of severed tissue inside of an access port in a patient's body with both ends of the suture material extending out of the access port. The surgeon then uses one end of the suture loop to tie a surgical slip knot around the other end of the suture loop. In order to facilitate tying, the slip knot is tied "extracorporeally," or outside of, the access port in the patient's body. A knot pusher can then be used to help advance the knot along one end of the suture loop while gently taking up the slack in the free end of the suture outside of the patient's body. This knot tying technique significantly reduces the time needed to close the incision and thus benefits both the patient and the surgeon.

Conventional knot pushers have included a V-shaped element, hook, or hole on the end of a long shaft. For example, a V-shaped element is included with a device available from Birtcher Solos while a device with a hole is available from Sharpe Endosurgical. Another approach uses a rod with a cone-shaped distal end having a hole which communicates between the front of the tip and a relieved section behind the tip. These devices have significant drawbacks in that they require the suture to either be threaded through a small hole or to be securely held within the crotch of the V-shaped element. The former configuration has been found difficult to set up while, in the latter configuration, the suture material often falls out of the V-shaped element. Furthermore, none of these conventional devices include a mechanism for cutting excess suture material away from the knot after the suture has been fully tightened.

SUMMARY OF THE INVENTION

The invention provides a surgical knot pusher which includes a shaft, a suture guide tip at a distal end of the shaft, an opening passing through a distal endwall of the tip for receiving and guiding suture material passing through the opening and suture attaching means for snap fitting suture material into the opening. The suture attaching means preferably comprises a slit in a sidewall of the tip. The opening can be circular and have a diameter which is larger than a width of the slit. The slit can be wider at a portion thereof adjacent an outer periphery of the sidewall to aid in aligning suture material with the slit.

According to a preferred embodiment, the tip can include a slot in a sidewall of the tip, the slot being in communication with the opening. The slot can include first and second channels which intersect each other, the first channel of said slot being arranged substantially parallel to a longitudinal axis of the shaft. The second channel can extend radially from one end of the first channel.

The surgical knot pusher can further comprise cutting means for cutting a suture in the slot. The cutting means can include a blade slidable in a bore in the tip for shearing suture material passing through the opening and into the bore. The shaft can comprise a tubular shaft and the cutting means can include a tubular cutter shaft slidable inside the tubular shaft, the tubular cutter shaft having a circular cutting blade at one end thereof and the opposite end of the tubular shaft extending outwardly beyond a proximal end of said tubular shaft. The surgical knot pusher can further comprise means for biasing the blade away from the tip.

BRIEF DESCRIPTION OF THE DRAWINGS

FIG. 3 schematically illustrates an enlarged cross-sectional side view of a rear portion of the device illustrated in FIG. 1;

FIG. 4 is an isometric view of the tip illustrated in FIG. 1; and

FIG. 5 is an enlarged end view of the tip illustrated in FIG. 4.

DETAILED DESCRIPTION OF THE PREFERRED EMBODIMENTS

Figure 1:
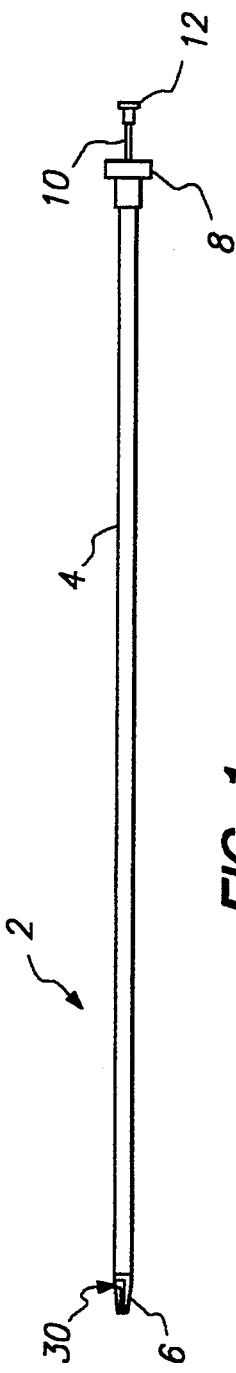
FIG. 1 is a side view of a device according to the present invention.

The present invention provides a surgical knot pusher which is easier to use than conventional knot pushing tools. In particular, the invention provides a surgical knot pusher which will reliably advance a surgical slip knot without allowing the suture material to slip out of the knot pusher. The term "suture" includes ligature and other filamentary material which may be used in a surgical procedure, such as laparoscopic surgery.

According to one aspect of the invention, a surgical knot pushing tool is provided having a tip which may be easily threaded and which can accommodate a wide range of suture material. According to another aspect of the present invention, a surgical knot pusher is provided which can precisely cut excess suture material from the tied knot. In addition, the present invention provides a surgical knot pusher which may be easily and inexpensively manufactured.

The present invention generally provides a surgical knot pusher that is reliable, simple to use, and, which after successfully advancing a knot, can optionally include means for cutting the suture material at a precise distance away from the knot. The device may include a shaft having a hollow conical distal tip which is slotted in a way to accept a variety of suture materials without damaging the material or allowing the suture to fall out of the tip.

The suture material is preferably snapped into place rather than having to be threaded through a hole. When combined with a cutting device, the inside of the shaft may contain an elongate member which has a sharp cutting edge on one end. The suture material can be cut by advancing the member towards the tip and a spring can be provided for biasing the member away from the tip. The tip may be formed from a resilient material which allows a slit in the tip to resiliently expand and thus permit various diameter suture materials to snap into an opening passing through the tip without letting them inadvertently slip out of the device.

The invention is now described with reference to an exemplary embodiment shown in the drawings. However, it will be apparent to those skilled in the art that the invention can be incorporated in other structures than those illustrated in the drawings.

Figure 2:
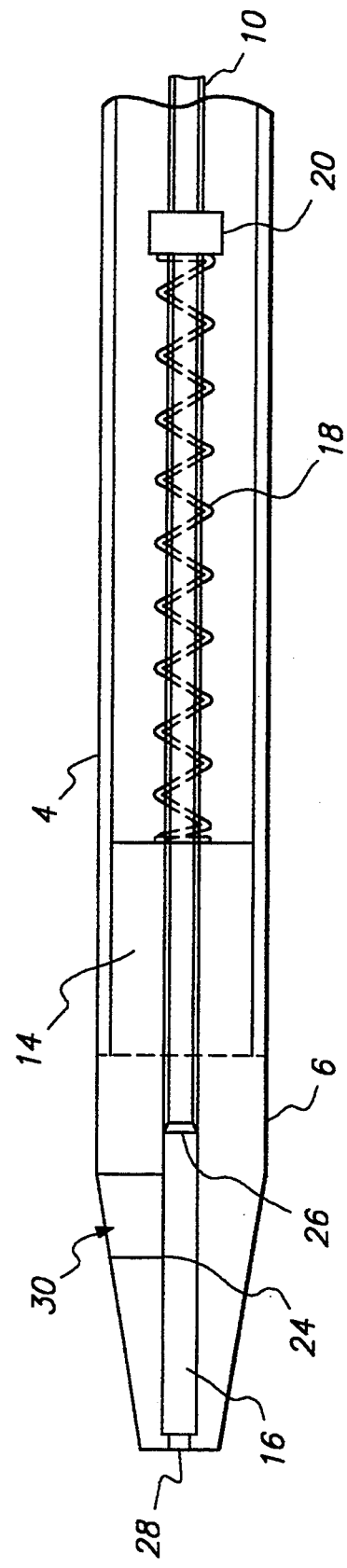
FIG. 2 schematically illustrates an enlarged cross-sectional side view of a front portion of the device illustrated in FIG. 1.

FIG. 1 is a side view of one embodiment of a surgical knot pusher 2 according to the present invention. The surgical knot pusher 2 includes a shaft 4 having a tip 6 at one end and a handle 8 at the other end. A suture cutting means comprising a cutter shaft 10 having a push knob 12 on one end and a cutting element (not shown in FIG. 1) on the other end, may be arranged to slide inside the shaft 4. As shown in FIG. 2, a coil spring 18 surrounds the cutter shaft 10 and is located between a spring stop 20 on the cutter shaft and the rear wall of the tip 6. The spring 18 biases a cutting blade 26 on a distal end of the shaft 10 away from the tip 6. A stop 22 on the shaft 10 is within shaft 4 and engages handle 8 to limit travel of shaft 10 in a direction away from the tip 6. However, the cutting means is optional and can be omitted from the surgical knot pusher 2.

The shaft 4 preferably comprises a tube of relatively stiff material in order to avoid undesirable flexing. Such material may include, but is not limited to, stainless steel, aluminum, engineered polymer materials such as polyetheretherketone, polyphenylene oxide, polyphenylene sulfide, and polymer composites such as glass-filled epoxy resin, carbon fiber-filled epoxy resin, and other suitable natural or synthetic resin materials known to those skilled in the art. The tip 6 can include a reduced diameter boss 14 which fits within the distal end of the tubular shaft 4. The tip also includes a central bore 16 for slidably receiving the cutting blade 26.

The cutting blade 26 is slidable into the bore 24 and preferably comprises a tubular member having a circular cutting edge at a distal end of the shaft 10. However, the blade 26 can have shapes other than circular and can be a separate piece which is attached to the end of the cutter shaft 10. Alternatively, the cutter shaft 10 and the blade 26 can be formed from a single piece of material such as stainless steel. The bore 16 in the tip 6 guides the blade 26 when the push knob 12 is moved toward the handle 8. However, other arrangements for the cutter shaft 10 and/or blade 26 may also be used.

FIG. 4 illustrates the tip 6 in more detail. The tip 6 preferably includes a substantially conical portion at a distal end thereof and a reduced diameter portion 14 at a proximal end thereof. The reduced diameter portion 14 fits within the distal end of the tubular body shaft 4 and can be attached thereto by any suitable means such as by adhesive, welding, etc. A small diameter suture guide opening 28 passes axially through the distal end wall of the tip and opens into the bore 24 which is larger in diameter than the opening 28.

In order to aid in threading suture material through the opening 28, a small slit 29 extends radially between the opening 28 and a sidewall of the tip 6. In addition, an L-shaped slot 30 is provided in the sidewall to accommodate an end of the suture prior to snapping that end of the suture material through the slit 29 and into the opening 28. The size and shape of the opening 28 and the slit 29 are preferably adjusted to allow suture material to be snapped sideways through the slit 29 and slide freely through the opening 28. The slit 29 should inhibit detachment of the suture material through the slit 29 during a knot pushing procedure wherein a knot in a first end of the suture material is advanced or pushed by the tip 6 along the second end of the suture material while the second end is pulled into the opening 28 and out of the slot 30. As illustrated in FIG. 5, the outer part of the slit 29 may be widened (e.g., notched or tapered) to aid in aligning and snapping the suture material through the slit 29 into the opening 28.

The opening 28 is preferably small enough to prevent a surgical slip knot in the suture material from passing through the opening 28 when the knot is pushed with the distal end wall of the tip 6. The portions of the sidewall of the tip 6 on either side of the slit 29 should be resilient enough to expand apart so that the suture material can be snapped through the slit 29 into the opening 28 without significantly damaging the suture material.

The slot 30 can be formed by cutting or grinding away part of the sidewall of the tip 6. For instance, the tip 6 can be ground along one side thereof until the bore 16 is exposed thus forming a longitudinally extending channel of the slot 30 and a radially extending channel of the slot 30 can be formed by grinding away a circumferential section of the sidewall adjacent a proximal end of the longitudinally extending channel. The channels can extend in any desired direction and/or intersect each other at any desired angle but in the arrangement shown, the longitudinally extending channel is parallel to the axis of the bore 16 and the radially extending channel is substantially perpendicular to the longitudinally extending channel.

The distal end of the tip 6 including the portion forming the opening 28 and the slit 29 cooperate to form a suture guide. However, the suture guide may include other arrangements for accommodating and guiding the suture material. The suture guide may also be formed from one or more pieces of the same or different materials.

The suture material can be passed axially along the bore 16 and outwardly of the tip 6 through the radially extending channel of the slot 30. The blade 26 can slide along the bore 16 and shear the suture material at the intersection of the two channels (i.e., at a shoulder 24 defining a common edge of the two channels). The blade 26 may also sever the suture material against the inner surface of the distal endwall of the tip in the case where the suture material extends outwardly of the bore 16 through the longitudinally extending channel of the slot 30. However, the suture can be cut at other locations depending upon the cutting mechanism used with the device.

The tip 6 preferably has sufficient strength and hardness to withstand the cutting action of the blade 26 without suffering significant damage due to contact with the blade 26. The tip 6 should also preferably exhibit sufficient flexibility and resiliency to allow a range of suture materials to be snapped through the slit 29 into the opening 28 without easily being dislodged from the suture guide 32. For example, sufficiently springy materials such as, but not limited to, superelastic nickel-titanium alloys, hard polyurethanes, nylons, polycarbonates, polyetheretherketones, ultrahigh molecular weight polyethylene, or suitable composite materials may be used. However, the tip 6 may be made of any material and can constitute a disposable and replaceable part of the device.

The blade 26 may be operated manually using push knob 12 or some suitable activation device may be incorporated to advance the cutter with a controlled cutting pressure. For example, an actuator disclosed in Waram, "Design Principles for Ni—Ti Actuators", Engineering Aspects of Shape Memory Alloys, at page 234, could be adapted for use with the present invention. In addition, the device could be actuated using a small battery to resistively heat a shape memory alloy element in order to actuate the blade 26.

The tip 6 may be manufactured by starting with a solid cylinder or truncated cone of suitable material such as plastic. The opening 28 is drilled through the distal end of the tip 6 along the central axis of the tip. The bore 16 is formed by drilling a hole sized to receive the tubular blade 26 in a proximal end of the tip, thus leaving a distal endwall with the opening 28 extending therethrough. The slot 30 is formed by cutting or grinding the sidewall of the tip 6 to form the two channels of slot 30. The tapered slit 29 may then be cut radially through the endwall to complete the suture guide. Alternatively, the tip 6 may be molded in one piece by injection molding or other suitable technique.

A reduced diameter boss 14 on the proximal end of the tip 6 is fastened inside the distal end of the tubular body shaft 4 permanently with a suitable adhesive or the boss can be threaded so as to be removably attached to the shaft 4. Coil spring 18 is slipped over a distal end of the cutter shaft 10 and the cutter shaft 10 and spring 18 are inserted through the proximal end of the tubular body shaft 4 with the blade 26 extending part-way into the bore 16 in the tip 6.

In normal operation of the surgical knot pusher device 2, a surgeon will have sewn a loop of suture material across an incision in a patient. The two loose ends of the suture material will extend outside the body of the patient so that a surgical slip knot in one end of the suture material can be loosely tied around the other loose end of the suture material. The loose end at a position above the knot is aligned with the notch in slit 29 and then snapped through the slit 29 into the opening 28 so that the surgical knot is placed in front of the opening 28 in the distal end of the tip 6. The surgical knot is then pushed against the tip 6 while the slack in the loose end is taken up through the opening 28 until the suture is tightly closed. The remaining suture material extending through opening 28 can then maneuvered into the radially extending leg of the slot 30 and the knob 12 can be depressed to cause the blade 26 to slide down the bore 16 and sever the suture material.

The principles, preferred embodiments, and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims.

What is claimed is:

1. A surgical knot pusher, comprising:
    a suture material a shaft;
    a suture guide tip at a distal end of the shaft, the suture guide tip including an opening passing through a wall of the suture guide tip for receiving and guiding the suture material passing through the opening; and
    the suture guide tip including snap fitting means for snap fitting the suture material into the opening said snap fitting means comprising a slit in a sidewall of the suture guide tip, the slit having a width smaller than a diameter of the suture material.

2. The surgical knot pusher as claimed in claim 1, wherein said suture guide tip includes a slot in a sidewall of the suture guide tip, the slot being in communication with the opening.

3. The surgical knot pusher as claimed in claim 2, wherein said slot includes first and second channels which intersect each other, the first channel of said slot being arranged substantially parallel to a longitudinal axis of said shaft.

4. The surgical knot pusher as claimed in claim 3, wherein the second channel extends radially from one end of the first channel.

5. The surgical knot pusher as claimed in claim 1, wherein said opening is circular and having a diameter which is larger than, the width of the slit.

6. The surgical knot pusher as claimed in claim 1, wherein said slit is tapered adjacent an outer periphery of the sidewall to aid in aligning suture material with the slit.

7. The surgical knot pusher as claimed in claim 1, further comprising cutting means for cutting a suture in said slot.

8. The surgical knot pusher as claimed in claim 7, wherein said cutting means includes a blade slidable in a bore in the suture guide tip for shearing suture material passing through the opening and into the bore.

9. A surgical knot pusher as claimed in claim 8, further comprising spring means for biasing the blade in a direction away from the suture guide tip.

10. A surgical knot pusher as claimed in claim 8, wherein the blade has a circular cutting edge.

11. The surgical knot pusher as claimed in claim 8, wherein the shaft comprises a tubular shaft and the cutting means includes a cutter shaft slidable inside said tubular shaft, said cutter shaft having said blade at one end thereof and another end of the cutter shaft extending outwardly from a proximal end of said tubular shaft.

12. A surgical knot pusher as claimed in claim 11, further comprising spring means for biasing said blade in a direction away from the suture guide tip.

13. A surgical knot pusher as claimed in claim 11, wherein the cutter shaft includes a handle for manually pressing the blade into the bore.

* * * * *